United States Patent [19]

Booher

[11] 4,376,860
[45] Mar. 15, 1983

[54] PYRIDYL KETONE

[75] Inventor: Richard N. Booher, Indianapolis, Ind.

[73] Assignee: Eli Lilly and Company, Indianapolis, Ind.

[21] Appl. No.: 325,517

[22] Filed: Nov. 27, 1981

[51] Int. Cl.³ .......................................... C07D 405/06
[52] U.S. Cl. .................................................... 546/268
[58] Field of Search ........................................ 346/268

[56] References Cited

U.S. PATENT DOCUMENTS 3,905,987  9/1975  Booher ............................ 260/296 R

OTHER PUBLICATIONS

Booher et al., *J. Med. Chem.* 20, 385–390, (1977).

*Primary Examiner*—Robert W. Ramsuer
*Attorney, Agent, or Firm*—Joseph A. Jones; Arthur R. Whale

[57] ABSTRACT

3-Pyridylcarbonyl-5-dioxane is a useful intermediate for preparing N,N-dialkyl-α-(3-pyridyl)-m-dioxane-5-methylamines, which are analgesics.

1 Claim, No Drawings

PYRIDYL KETONE

BACKGROUND OF THE INVENTION

1. Field of the Invention

This invention concerns the field of pharmaceutical chemistry, and provides a useful intermediate compound used in the preparation of known analgesics which are N,N-dialkyl-α-(3-pyridyl)-m-dioxane-5-methylamines.

2. State of the Art

The analgesics which are the ultimate products prepared from the intermediate of this invention were disclosed by Booher in U.S. Pat. No. 3,905,987. Booher taught intermediates related to the compound of this invention, but stated that the process which would use the present intermediate for making pyridyl-substituted analgesics was not effective, and so he taught that there was no motive to make the present intermediate.

SUMMARY OF THE INVENTION

This invention provides the pyridylcarbonyldioxane of the formula

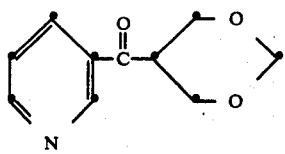

DESCRIPTION OF THE PREFERRED EMBODIMENTS

In this document, all temperatures are expressed in degrees Celsius.

The compound of this invention is prepared by methods analogous to those taught by Booher, cited above. Preferably, 3-acetylpyridine is condensed with a polymer of formaldehyde in the presence of boron trifluoride. The condensation goes best in an acid reaction mixture, preferably with acetic acid or another alkanoic acid as the solvent. It is most preferred to use about 2-4 moles of boron trifluoride etherate, especially about 3 moles, and about 2-5 moles of paraformaldehyde, especially about 3-4 moles, at temperatures in the range of about 50°-80°, especially about 50°-70°.

A preferred synthesis of the compound is shown below as Example 1.

An alternative synthesis of the pyridylcarbonyldioxane is the reaction of 5-cyano-m-dioxane with 3-lithiopyridines. The reaction is analogous to a Grignard reaction, and is preferably run in an ether, especially diethyl ether or tetrahydrofuran, at low temperatures in the range of from about −100° to about 0°, preferably from about −80° to about −20°.

The 5-cyano-m-dioxane used above is prepared by the condensation of a polymer of formaldehyde with a substituted propanediol of the formula

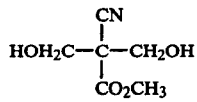

to obtain a dioxane of the formula

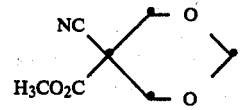

The condensation is carried out in the presence of boron trifluoride or strong organic acid such as methane- or toluenesulfonic acid.

The dioxane above is then decarboxylated, as by water-dimethyl sulfoxide, according to the method of Krapcho et al., *J. Org. Chem.* 43, 138–46 (1978).

The compound of this invention is used in a synthesis of pyridyl-dioxane analgesics, which are described in the Booher patent cited above. It should be noted that the process is used only to prepare those of Booher's compounds which have alkyl groups on the amino nitrogen. The first step of the process is the reaction of the pyridylcarbonyldioxane with a secondary amine having the substituents of the desired analgesic to form the enamine intermediate. The process is carried out in the presence of titanium tetrachloride. The preferred amount of titanium tetrachloride is in the range of from about 0.5 mole per mole of starting compound to about 0.8 mole per mole of starting compound. It is most preferred to use from about 0.5 to about 0.6 mole of titanium tetrachloride per mole of starting compound, but it will be understood that the optimum amount of the catalyst will vary, depending on the compound being prepared and other factors.

It is usually advisable to use a substantial excess of the secondary amine reactant, in the range of about 3–6 moles per mole of the dioxane, more preferably about 5–6 moles.

It is preferred to conduct the enamine reaction in benzene or toluene, which have been found to facilitate the simple isolation of the enamine for the next step. Xylene is somewhat less preferred as a solvent. The process can be carried out in other solvents as well as in the preferred solvents, including such commonly used inert reaction solvents as halogenated solvents including dichloromethane, chloroform, chlorobenzene, and the various dichlorobenzenes and chlorotoluenes.

The enamine reaction gives economically complete yields in relatively short periods of time. It has been found advantageous to use a period of 30 minutes at about 0° followed by 30 minutes at ambient temperature. Temperatures from about −25° to about ambient temperature may be used; it is more preferred to use temperatures from about −10° to about 20° while the reactants and the catalyst are being combined; the reaction mixture may be warmed to about ambient temperature after it is complete in the preferred practice of this invention. Higher temperatures, above ambient temperature, may be used if desired but are likely to result in depressed yields.

The enamine is reduced by any convenient means to form the desired product. It is not necessary to purify the enamine before reducing it; adequately pure enamine is obtained by merely filtering the titanium dioxide and amine hydrochloride out of the reaction mixture, and evaporating the filtrate to dryness.

Conventional reduction methods, such as are commonly used for the reduction of enamine compounds in general, work quite well in this process. For example, a preferred method of reduction is hydrogenation in the presence of a noble metal catalyst, especially a platinum catalyst on a carbon carrier. Palladium catalysts are also quite effective; other commonly used hydrogenation catalysts, such as iridium, ruthenium and the like may be employed in the conventional manner. Relatively low hydrogen pressures, in the range of about 1–5 atmospheres, are quite adequate. As usual, the common inert reaction solvents may be used for hydrogenations, especially alkanols.

Another preferred exemplary method of reduction is by means of a hydride, especially a borohydride or cyanoborohydride. More particularly, sodium borohydride and sodium cyanoborohydride are preferred reducing agents. Other common reducing agents can also be used, however, such as lithium aluminum hydride, sodium bis(2-methoxyethoxy)aluminum hydride and the like.

It is preferred to use a substantial excess of a chemical reducing agent, in the range of from about 2 to about 6 moles per mole of enamine. However, an amount approximating the stoichiometric amount, or a large excess, even up to 10 moles or more, may also be used.

Chemical reductions are carried out in an acid environment, and it is preferred to use a small amount of acetic acid in the mixture. Whether acetic is used or some other acid, it is necessary only to add a sufficient amount of acid to assure that the mixture is acidic during the reduction. Amounts in the range of from about the stoichiometric amount to about 2 or 3 moles per mole of enamine are adequate.

In general, reductions are carried out in an inert organic solvent. Any appropriate solvent may be used, of which alkanols, especially methanol, ethanol and propanol, are preferred. Other inert organic solvents such as were discussed above may be used, however, as may be appropriate in a given situation.

Typically chemical reductions are carried out at about ambient temperature; the temperature at which this step is performed, however, may be varied over a wide range, as may be convenient in the circumstances.

EXAMPLE 1

5-(3-Pyridylcarbonyl)-m-dioxane

A 60.6 g. portion of 3-acetylpyridine was combined with 54 g. of paraformaldehyde and 250 ml. of acetic acid. The mixture was cooled in an ice bath, and 184 ml. (1.5 moles) of boron trifluoride etherate was added dropwise with stirring, over a period of about 40 minutes. The temperature of the mixture ranged from 15° to 26° during the addition. The mixture was then stirred under reflux, at about 67°, for 2 hours 15 minutes, and was then cooled slightly. The volatile portions and most of the acetic acid were removed under vacuum, and the remaining mixture was rinsed with water to a large beaker and was made basic with ammonium hydroxide. The basic mixture was filtered through glass wool, and the filtrate was extracted with chloroform. The organic layer was then washed with saturated aqueous sodium chloride, and was dried over magnesium sulfate and filtered. The filtrate was evaporated under vacuum to obtain 128 g. of crude product, which was recrystallized from isopropanol. The total yield was 59.1 g. of purified product, the first crop of which had a melting point of 98°–100°.

EXAMPLE 2

5-(3-pyridylcarbonyl)-m-dioxane

A 48.4 g. portion of 3-acetylpyridine was combined with 60 g. of paraformaldehyde and 200 ml. of glacial acetic acid, and to the mixture was added, dropwise with stirring, 86 g. of boron trifluoride etherate. The mixture was then heated, and was stirred under reflux for 4 hours. The reaction was cooled and the volatile materials were evaporated under vacuum to obtain 60 g. of an oily yellow solid, which was crystallized by the addition of water. The solids were separated by filtration, washed with water and dried to obtain 25 g. of the desired product, m.p. 91°–100°.

The filtrate was evaporated to dryness under vacuum, and the solid residue was triturated with 100 ml. of isopropanol. The isopropanol was evaporated under vacuum to obtain 10 g. of impure product. The two portions of product were combined and recrystallized from 150 ml. of isopropanol to obtain 30 g. of purified product, m.p. 99°–100°.

PREPARATION 1

5-(3-Pyridyl)(dimethylamino)methylene-m-dioxane

Ten g. of the ketone of Example 1 was added to a flask and dissolved in 150 ml. of benzene. The solution was cooled to 5°–10°, and 20.6 ml. of dry dimethylamine was added. A cold solution of 3.4 ml. of titanium tetrachloride in 50 ml. of benzene was added dropwise with stirring while the reaction mixture was maintained at a temperature below 20°. When the addition was complete, the mixture was stirred in an ice bath for 30 minutes, and then at ambient temperature for 30 minutes more. The mixture was then filtered and the filter cake was washed with benzene. The filtrate was then evaporated under vacuum to obtain a viscous residue weighing 10.8 g. Nuclear magnetic resonance analysis of the residue in CDCl$_3$ showed characteristic peaks at δ2.77 (s, 6H); 4.12 (s, 2H); 4.68 (s, 2H); and 4.99 (s, 2H); indicating the presence of the desired enamine.

PREPARATION 2

N,N-Dimethyl-α-(3-pyridyl)-m-dioxane-5-methylamine

A 5.19 g. portion of the enamine prepared above was dissolved in 65 ml. of denatured ethanol, and combined with 0.52 g. of 5% platinum on carbon hydrogenation catalyst in a low pressure hydrogenation vessel. The system was flushed with hydrogen and then charged with hydrogen at 3.8 kg./cm.$^2$. The vessel was shaken at ambient temperature for 5.5 hours, after which the pressure had dropped by 0.35 kg./cm.$^2$. The mixture was then removed from the vessel and filtered, and the filtrate was evaporated under vacuum to obtain 5.08 g. of viscous oil, which was identified by nmr analysis in CDCl$_3$ as follows: δ8.21 (m, 2H), 7.35 (m, 2H); 4.91 (d, 1H); 4.63 (d, 1H); 2.10 (s, 6H).

I claim:

1. The pyridylcarbonyldioxane of the formula

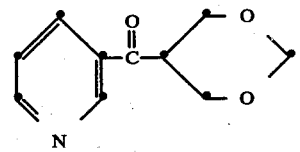

* * * * *